United States Patent [19]

Cooper et al.

[11] Patent Number: 4,662,030
[45] Date of Patent: May 5, 1987

[54] VISCOSITY CONTROL

[76] Inventors: Albert A. Cooper, 1, Wolsey Road, Hemel Hempstead, Hertfordshire, HP2 4TU, United Kingdom; Gerald N. Shields, 3705 N. Lincoln Ave., Chicago, Ill. 60613

[21] Appl. No.: 797,185

[22] Filed: Nov. 12, 1985

Related U.S. Application Data

[63] Continuation of Ser. No. 576,151, Feb. 2, 1986, abandoned.

[30] Foreign Application Priority Data

Feb. 3, 1983 [GB] United Kingdom .................. 8302938
Jan. 31, 1984 [EP] European Pat. Off. ....... 84.300612.3

[51] Int. Cl.$^4$ ............................................ G01N 11/12
[52] U.S. Cl. .......................................... 73/56; 73/57; 73/224
[58] Field of Search .................................... 73/54–57, 73/224, 861.51

[56] References Cited

U.S. PATENT DOCUMENTS

| | | | |
|---|---|---|---|
| 31,100 | 1/1861 | Adams | 73/56 X |
| 174,240 | 2/1876 | Hicks | 73/56 X |
| 1,840,101 | 1/1932 | Jespersen | 73/56 X |
| 2,092,223 | 9/1937 | Payne | 265/11 |
| 2,141,329 | 12/1938 | Zahn | 73/56 |
| 2,262,573 | 11/1941 | Bender | 137/78 |
| 2,309,910 | 2/1943 | Kott | 265/11 |
| 2,314,822 | 3/1943 | Quesada | 137/78 |
| 2,314,991 | 3/1943 | Knauth | 265/11 |
| 2,320,720 | 6/1943 | Croft | 265/45 |
| 2,343,030 | 2/1944 | Simmons | 265/11 |
| 2,426,393 | 8/1947 | Fischer | 73/56 |
| 2,437,715 | 3/1948 | Thorp et al. | 92/46 |
| 2,564,892 | 8/1951 | Gerin | 73/56 |
| 2,587,174 | 2/1952 | Lantz | 137/78 |
| 2,590,538 | 3/1952 | Huck | 137/78 |
| 2,668,441 | 2/1954 | Peterson | 73/56 |
| 2,707,916 | 5/1955 | Smith et al. | 101/363 |
| 2,969,016 | 1/1961 | Crosfield et al. | 101/202 |
| 3,071,961 | 1/1963 | Heigl et al. | 73/55 |
| 3,187,563 | 6/1965 | Tobias | 73/56 |
| 3,308,843 | 3/1967 | Hollis et al. | 137/92 |
| 3,344,799 | 10/1967 | Hardin | 137/92 |
| 3,508,566 | 4/1970 | Stumm | 73/56 X |
| 3,526,126 | 9/1970 | Wilchinsky et al. | 73/56 |
| 3,557,817 | 1/1971 | Royse | 137/91 |
| 3,596,672 | 8/1971 | McBee | 137/92 |
| 3,605,782 | 9/1971 | Hollis et al. | 137/91 |
| 3,625,050 | 12/1971 | Noetzel et al. | 73/56 |
| 3,667,500 | 6/1972 | Stone | 137/386 |
| 3,712,117 | 1/1973 | Fitzgerald et al. | 73/59 |
| 3,734,119 | 5/1973 | Nudds | 137/92 |

(List continued on next page.)

FOREIGN PATENT DOCUMENTS

| | | | |
|---|---|---|---|
| 2044356 | 9/1970 | Fed. Rep. of Germany | |
| 2214758 | 10/1973 | Fed. Rep. of Germany | 73/55 |
| 2253409 | 6/1975 | France | 73/55 |
| 2333233 | 6/1977 | France | 73/56 |
| 393793 | 11/1965 | Switzerland | 73/56 |

Primary Examiner—Robert Spitzer
Attorney, Agent, or Firm—Wood, Dalton, Phillips, Mason & Rowe

[57] ABSTRACT

A viscosimeter comprising a Zahn cup, a supply tank arranged to supply a liquid, the viscosity of which is to be measured, to the Zahn cup, a control mechanism operable to stop the supply of liquid to the Zahn cup once the latter has been filled to overflowing, and a timing mechanism arranged to measure the time taken for the Zahn cup to empty following operation of the control mechanism. The timing mechanism comprises an emitter-detector pair positioned to direct a sensing beam across the flow path of liquid which leaves the Zahn cup and a timer connected to commence a time measurement at the instant of operation of the control mechanism, and to stop the measurement at the instant the detector of the emitter-detector pair indicates an absence of liquid therebetween.

Such a viscosimeter may be used in the measurement of the viscosity of ink used in a printing process, and the control of the viscosity in dependence upon that measurement.

15 Claims, 8 Drawing Figures

U.S. PATENT DOCUMENTS

| | | | |
|---|---|---|---|
| 3,782,173 | 1/1974 | Van Vessem et al. | 73/56 |
| 3,832,886 | 9/1974 | Pliskin | 73/56 |
| 3,869,984 | 3/1975 | Toth | 101/349 |
| 3,901,149 | 8/1975 | Schulte-Kulkmann | 101/349 |
| 3,908,441 | 9/1975 | Virloget | 73/55 |
| 3,973,491 | 8/1976 | Porth et al. | 101/124 |
| 4,065,959 | 1/1978 | Richardson | 73/56 |
| 4,130,126 | 12/1978 | Chocholaty et al. | 137/3 |
| 4,154,195 | 5/1979 | Mugrauer | 118/659 |
| 4,190,846 | 2/1980 | Yamamoto et al. | 346/140 R |
| 4,276,383 | 6/1981 | Leighton et al. | 73/57 X |
| 4,333,336 | 6/1982 | Myerholtz et al. | 73/56 |
| 4,362,179 | 12/1982 | MacPhee | 137/3 |
| 4,400,973 | 8/1983 | Hegedus | 73/56 |
| 4,426,878 | 1/1984 | Price et al. | 73/56 X |
| 4,432,761 | 2/1984 | Dawe | 73/55 X |
| 4,466,275 | 8/1984 | Thöne | 73/57 |

VISCOSITY CONTROL

This is a continuation of co-pending application Ser. No. 576,151 filed on Feb. 2, 1984, now abandoned.

BACKGROUND OF THE INVENTION

The present invention, in one of its aspects, relates to a viscosimeter comprising a Zahn cup, supply means arranged to supply a liquid, the viscosity of which is to be measured, to the Zahn cup, control means of the supply means operable to stop the supply of liquid to the Zahn cup once the latter has been filled to overflowing, and timing means arranged to measure the time taken for the Zahn cup to empty following operation of the said control means.

Thus the present invention relates to viscosity measurement, more especially, but not exclusively, to the measurement of the viscosity of ink used in a printing process, and the control of the viscosity in dependence upon that measurement. The invention is applicable to the measurement and control of the viscosity of any fluid where such control may be effected by the addition of a viscosity-changing fluid.

Hitherto, such measurement and control has been effected automatically by positioning an upper outlet and a bottom outlet of a Zahn cup above respective levers of a switching arrangement. The cup is filled, and the time between the successive instants when the two levers no longer have fluid impinging upon them is measured to provide a value of the viscosity of the fluid. This involves a complex construction of levers, pivoting means therefor, and means to detect the positions of the levers so as to determine whether or not liquid is impinging on them.

The present invention seeks to simplify measurement of the viscosity of a liquid using less complex means to measure the time taken for fluid to flow out from the Zahn cup.

SUMMARY OF THE INVENTION

Accordingly, a first aspect of the present invention is directed to a viscosimeter having the constructions set out in the opening paragraph of the present Specification, characterized in that the timing means comprises an emitter-detector pair positioned to direct a sensing beam across the flow path of liquid which leaves the Zahn cup, and a timer device connected to commence a time measurement at the instant of operation of the control means, and to stop the measurement at the instant the detector of the emitter-detector pair indicates an absence of liquid therebetween.

The present invention also extends to a method of measuring the viscosity of a liquid comprising supplying liquid to a Zahn cup until the latter overflows, stopping the liquid supply and measuring the time taken for liquid to flow out from the cup, characterised in that the time measurement commences at the instant when the liquid supply is stopped, and ends at the instant when the flow of liquid from the Zahn cup ceases as detected by an emitter-detector pair positioned to direct a sensing beam across the flow path of liquid which leaves the Zahn cup.

According to another aspect of the present invention, there is provided a viscosimeter comprising a Zahn cup, supply means arranged to supply a liquid, the viscosity of which is to be measured, to the Zahn cup, control means of the supply means operable to stop the supply of liquid to the Zahn cup, and timing means arranged to measure the time taken for liquid to flow out from the Zahn cup following operation of the said control means, characterised in that the timing means comprises a float within the cup, and a timer device connected to measure the time taken by the float to drop through a predetermined distance.

In one application of the present invention, the viscosity of ink used in a printing process is maintained at a desired level. In this case, the aforesaid main fluid is the ink, and the viscosity-changing fluid is the solvent, in pure form, which is present in the ink solution. In this application, solvent is added to the ink in a controlled manner to counter thickening of the ink which occurs owing to evaporation of the solvent from the ink.

BRIEF DESCRIPTION OF THE DRAWINGS

An example of apparatus made in accordance with the present invention is illustrated in the accompanying drawings, in which.

DETAILED DESCRIPTION OF THE PREFERRED EMBODIMENT

Figure 1:
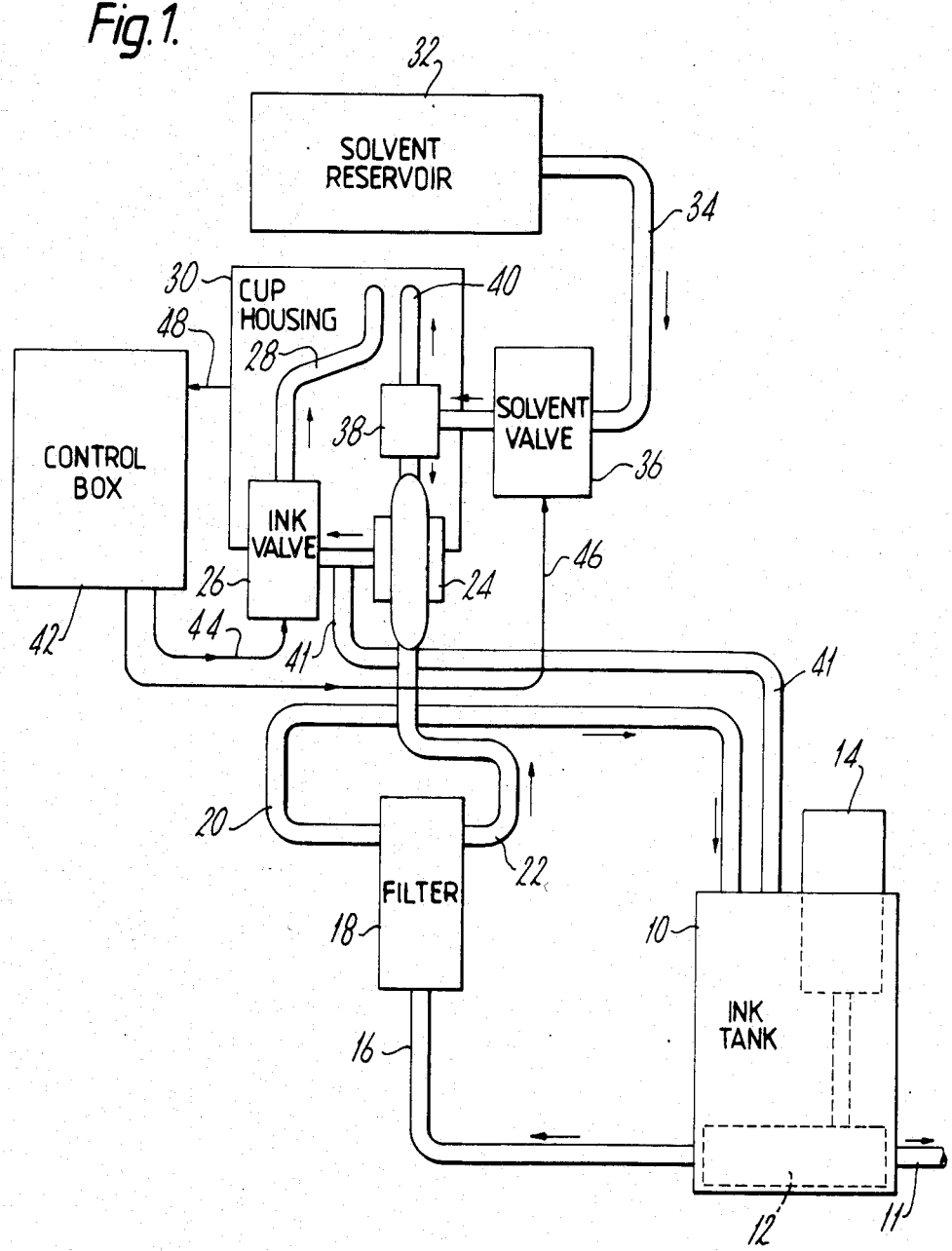
FIG. 1 is a rear diagrammatic view of the apparatus.

FIG. 1 shows an ink tank 10 containing ink which flows out from the tank through a main outlet 11 to printing apparatus (not shown). The tank is provided with a centrifugal pump 12, driven by a motor 14, to agitate the ink in the tank and also to provide pressure to urge the ink in the tank along a delivery tube 16 to a filter 18. A first outlet from a filter 18 is an overflow or surplus tube 20 which returns to the ink tank 10, and the second output from the filter 18 is a further delivery tube 22 which extends to a three-port two-way valve 24. An outlet from this valve 24 is connected to an inlet of a normally-open solenoid ink valve 26 the outlet of which is connected to a feed pipe 28 which passes through the rear of a cup housing 30 into the interior thereof. The apparatus further comprises a solvent reservoir 32 which contains solvent, in neat form, which is the same fluid as is contained in the ink solution. A gravity feed tube 34 extends downwardly from the outlet of the reservoir 32 to a normally closed solenoid solvent valve 36. The output of the latter is connected to a T-junction 38 from which solvent may flow downwardly to the two-way valve 24, or upwardly through a solvent feed pipe 40 which passes through the rear of the cup housing 30 into the interior thereof. Fluid is returned from the cup housing via a return tube 41 to the ink tank 10.

A control box 42 has respective outputs connected via lines 44 and 46 respectively to control the solenoids of the ink valve 26 and the solvent valve 36. An output from an emitter-detector pair (not shown in FIG. 1) within the housing 30 is connected via a line 48 to an input of the control box 42.

Figure 2:
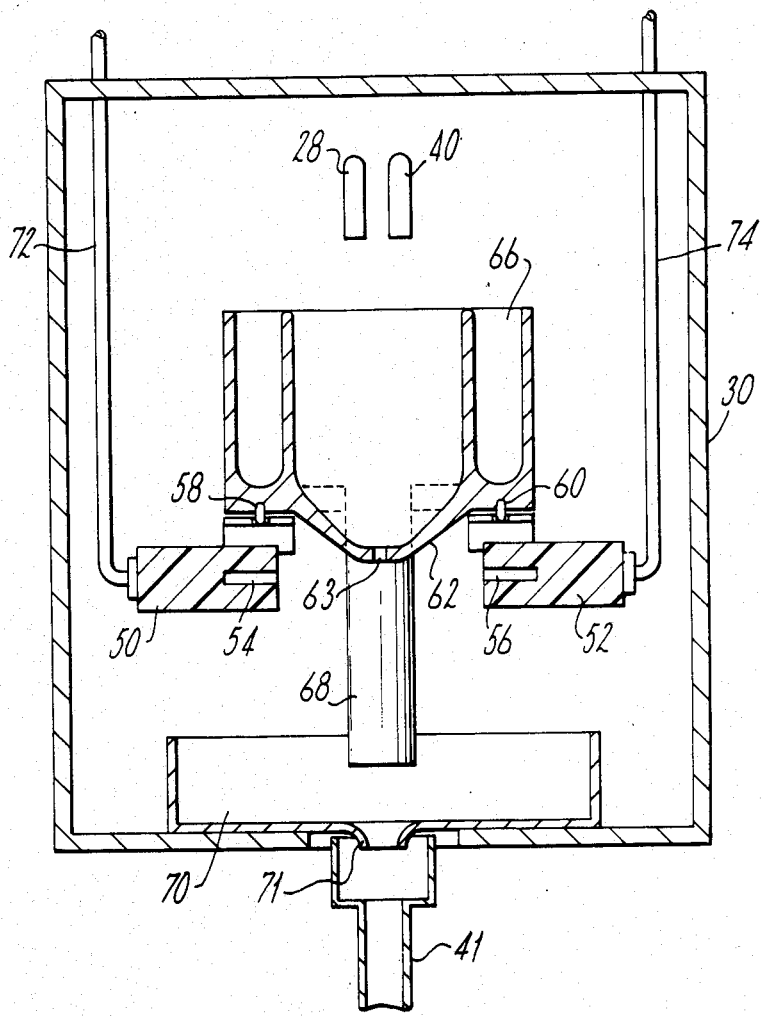
FIG. 2 is a front cross-sectional view of a cup housing of the apparatus shown in FIG. 1.
Figure 3:
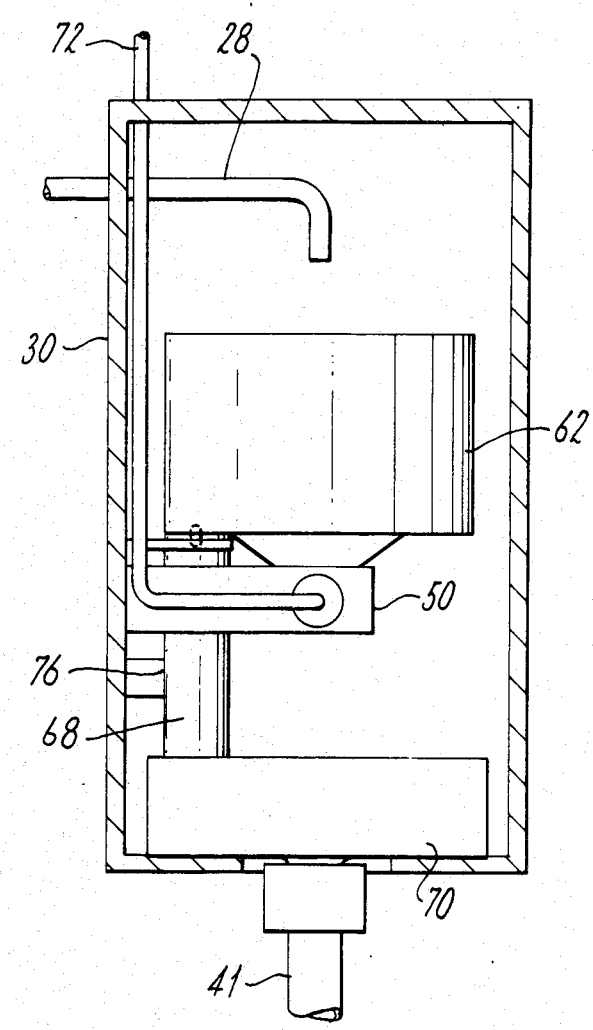
FIG. 3 is a diagrammatic side view of the cup housing shown in FIG. 2.
Figure 4:
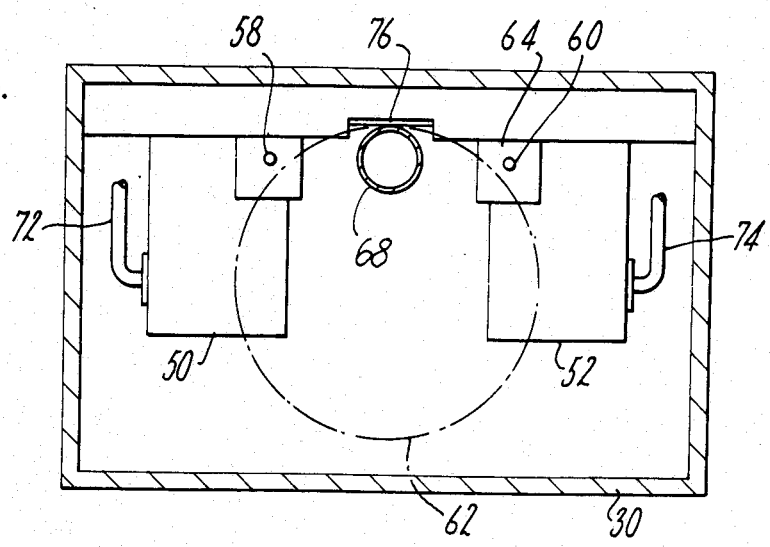
FIG. 4 is a diagrammatic plan view of the cup housing shown in FIGS. 2 and 3, with the cup shown in ghost form only.

The cup housing and its contents are shown more clearly in FIGS. 2 to 4. It contains two mounting blocks 50 and 52 secured to a rear wall of the housing 30 and in which are embedded an emitter-detector pair 54 and 56 respectively. Two locating spigots or dowels 58 and 60 are provided in the Zahn cup 62. A B4 cup 62 having a lower conical portion provided with an orifice 63 through the bottom thereof is supported mainly above the mounting blocks 50 and 52 by means of a mounting bracket which receives the locating spigots or dowels 58 and 60 respectively. A deep annular trough, gutter or channel 66 is provided around the side of the cup 62 to receive any fluid which overflows from the cup. A drain pipe 68 which is in communication with the channel 66, extends downwardly from an intended rear part of the cup 62. A recess 76 in the rear wall of the housing 30 provides an abutting surface at a position below the level of the spigots 58 and 60 to prevent the cup from toppling over, and also, in combination with the locating spigots 58 and 60, to position the cup in a precise manner to ensure that the orifice 63 is directly above the path extending between the emitter 54 and the detector 56. In this position, the cup 62 is positioned directly underneath the feed pipes 28 and 40 for the ink and solvent respectively, and the drain pipe 68 and orifice 63 are arranged above a collecting tray 70 which rests on the bottom of the housing 50 and has a central outlet 71 positioned over the mouth of the return tube 41.

Respective power lines 72 and 74 provide electrical power for the emitter-detector pair 54 and 56.

The emitter-detector pair 54 and 56 are, in this instance, an infra-red emitter and detector, although it will be appreciated that other emitter-detector pairs could be used instead.

Figure 5:
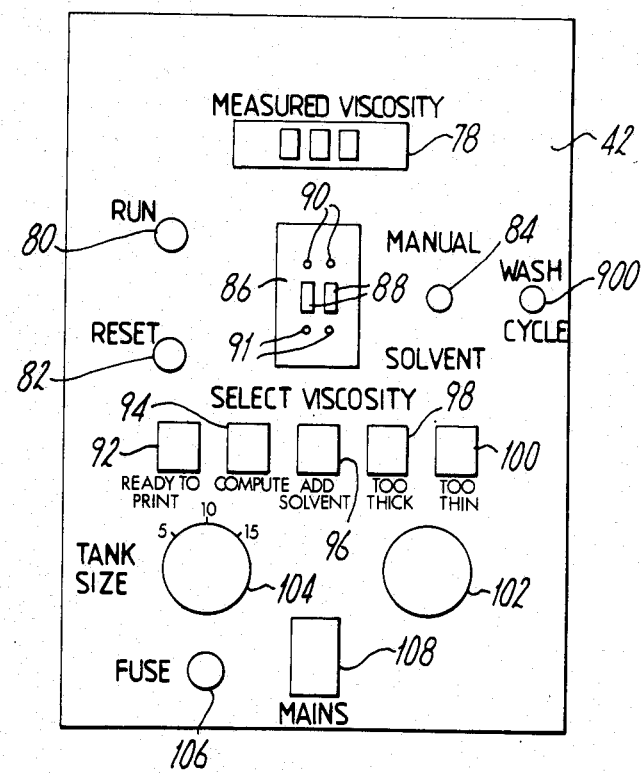
FIG. 5 is a front view of a control box shown in FIG. 1.

FIG. 5 shows a control panel on the front face of the control box 42 shown in FIG. 1. The control panel comprises a measured viscosity three-digit display 78, to show the actual value of the ink as measured by the apparatus, push-buttons 80, 82 and 84 for entering the commands "run", "reset", and "manual solvent", respectively for starting operation of the apparatus, resetting any values already retained in the computer memory, and to flush solvent through the apparatus (overriding any other operating condition of the apparatus). The display panel further comprises indicator lamps 92, 94, 96, 98 and 100 to indicate respectively when the apparatus is ready to print, when it is computing, when the solvent is to be added to the ink, when the ink is too thick, and when the ink is too thin. The display panel also has a tank size setting knob 104 for setting the apparatus to operate appropriately for a tank size of 5 gallons, 10 gallons or 15 gallons. There is also an alarm 102, an accessible fuse 106, and a mains switch 108.

Figure 6:
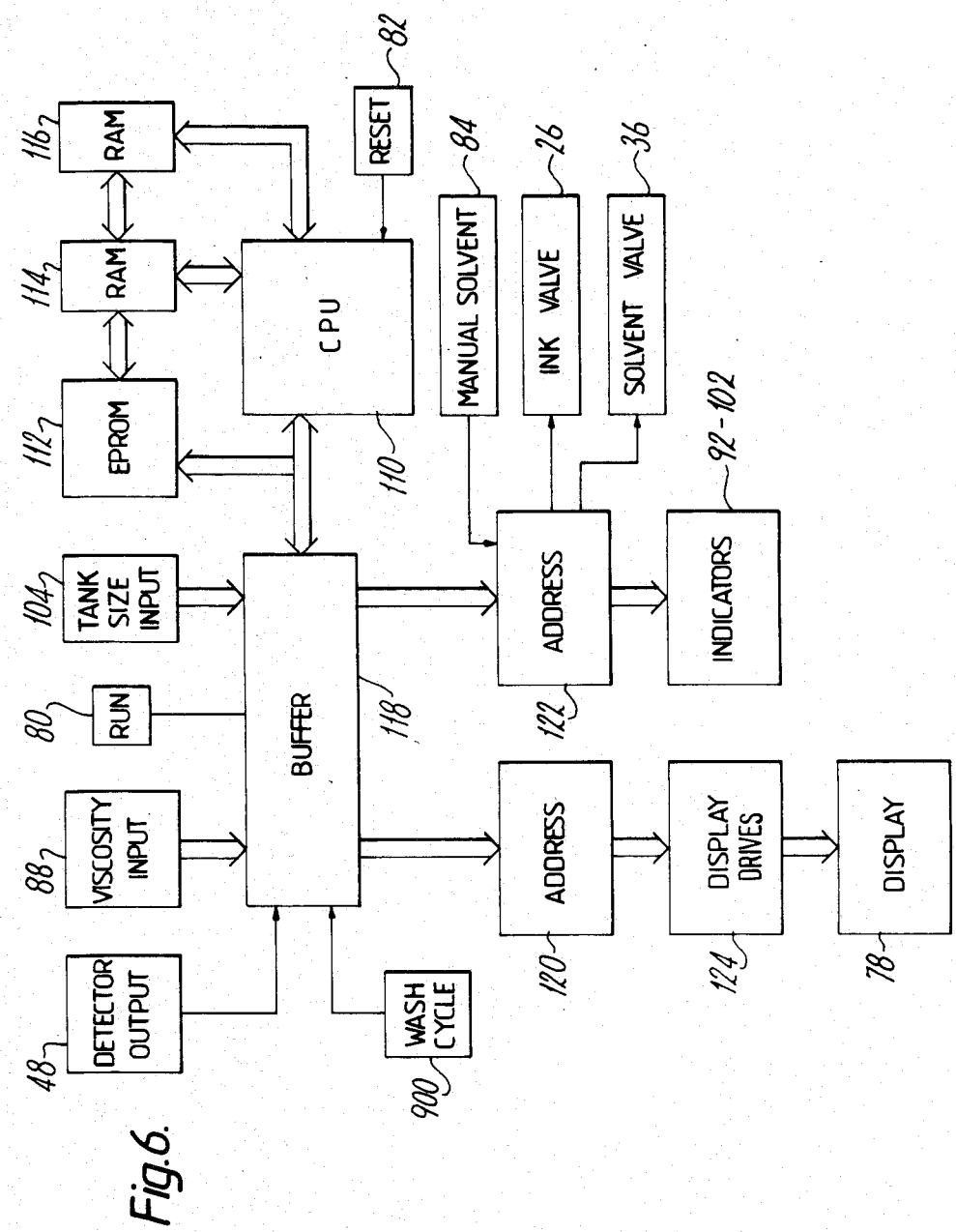
FIG. 6 is a box circuit diagram of the electronic circuitry used in the control box of FIG. 1.

FIG. 6 shows the electronic circuitry contained in the control box 42 for controlling operation of the apparatus. This comprises a central processing unit 110 pre-programmed to effect the desired control, associated memories in the form of an EPROM 112 and two RAMs 114 and 116 connected to communicate with the central processing unit 110 and with one another. The circuitry further comprises a buffer 118 connected to communicate with the central processing unit 110 and to act as an interface between that unit and any electrical signals from the detector output 48, the viscosity input 88, the run push-button 80, and the tank size input 104. Outputs from the buffer 118 control, via an address 120, the display drives 124 of the viscosity display 78. The buffer 118 also controls the ink valve 26 and the solvent valve 36 via a further address 122, which also operates the indicators 92 to 102. The reset button 82 is connected directly to an input of the central processing unit 110, and the manual solvent push button 84 is also connected to the CPU 110 via the address 122 and buffer 118.

Figure 7:
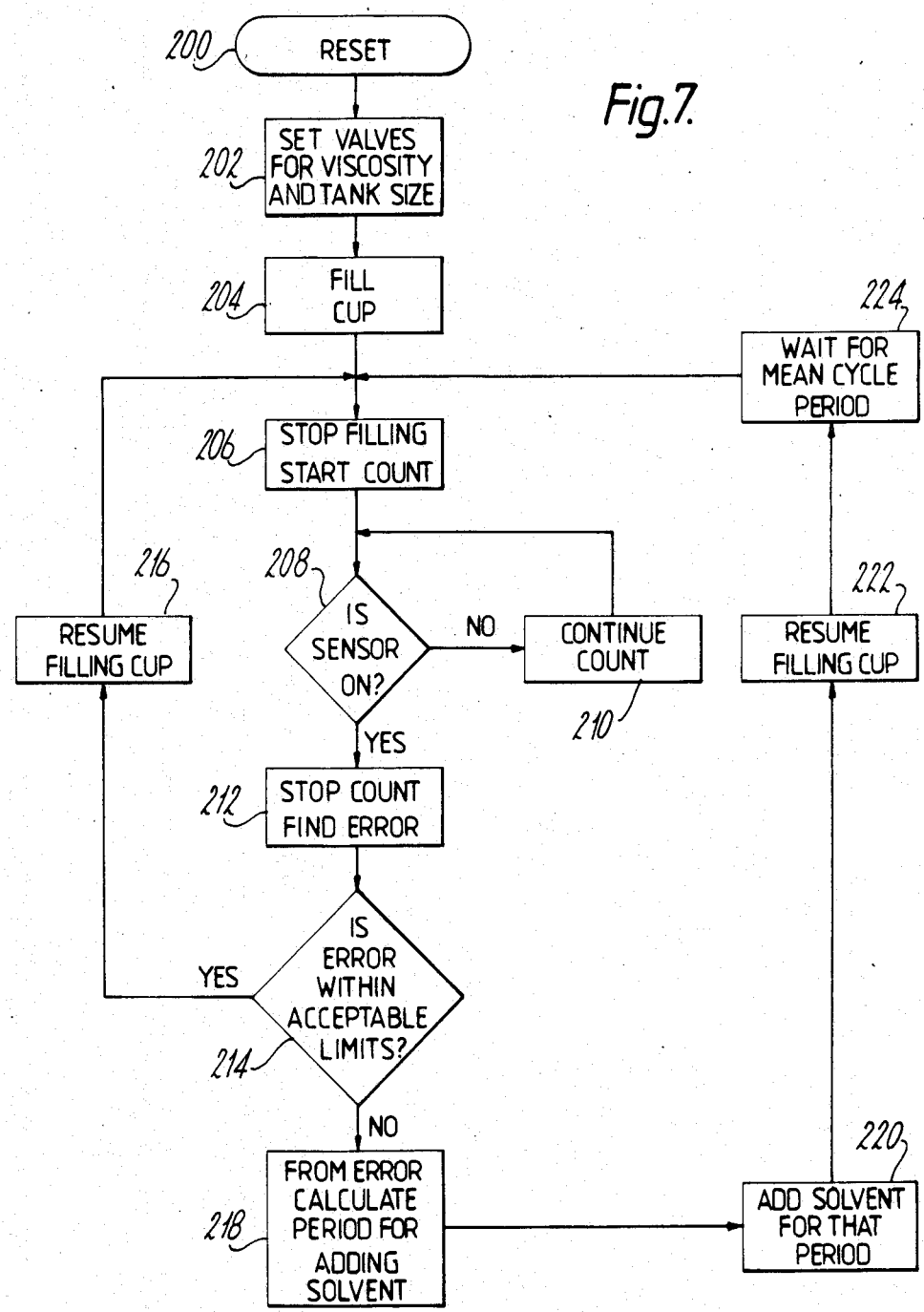
FIG. 7 is a flow chart of the operation of the apparatus.

Operation of the apparatus will now be described with reference to FIG. 7. With the main switch 108 (shown in FIG. 5) switched on, the reset button 82 is depressed to clear any values for the time being held in any of the memories of the electronic circuitry. This is represented by the first step labeled "RESET" in the first step 200 in FIG. 7. The values for the desired viscosity and the tank size used are then set, as indicated by step 202 in FIG. 7, by means of the select viscosity subpanel 86 and the tank size knob 104. Since the ink valve 26 shown in FIG. 1 is normally open, ink flows from the tank 10, under the pressure exerted by the centrifugal pump 12 driven by the motor 14, through the delivery tube 16 to the filter 18 where it is filtered. From there it continues to flow through the tube 22 to the 2-way valve 24, through the ink valve 26 to the feed pipe 28 from which it falls into the cup 62 through the orifice 63 into the collecting tray 70 and down into the return tube 41 back to the ink tank 10. Since the orifice 63 is comparatively small, ink cannot flow through that orifice as quickly as it can flow through the feed pipe 28. As a result, if the cup 62 is not already full it will quickly fill until the ink overflows into the channel 66 down the drainpipe 68 to the tray 70 shown in FIG. 2. In this way the "FILL CUP" step 204 shown in FIG. 7 is completed. After a predetermined time has elapsed from depression of the "RUN" button 80, the central processing unit 110 sends a command signal via the buffer 118 and the address 122 to close the ink valve 26. All the ink flowing through the delivery tube 16 to the filter 18 will now return to the ink tank via the excess or overflow tube 20 as shown in FIG. 1. At the very instant the ink valve 26 is closed, the unit 110 starts to count. Thus step 206 in FIG. 7 is accomplished, immediately after which the unit 110 continuously asks whether the sensor, comprising the emitter and detector pair 54 and 56, is on. If ink is still flowing from the cup 62 through the orifice 63, the flow of ink from that orifice will block the path of radiation from the emitter 54 to the detector 56 and the sensor will not be on. In that case, the unit 110 will continue its count so that the apparatus proceeds with the loop indicated by steps 208 and 210 in FIG. 7. As soon as a signal is received from the detector output 48 the count is stopped and its value displayed on the viscosity display 78. The rate at which the unit 110 counts is determined so that this display is in the form of "Zahn two" seconds which is an indication of the time which the same ink would take to empty through the orifice of a "Zahn cup", the latter being a cup of standard size having a standard orifice in its bottom. Since the rate at which ink can flow through a small orifice is dependent upon its viscosity, this count provides a direct measure of the actual viscosity of the ink. The unit 110 now compares this actual value with the desired value entered on the select viscosity subpanel 86, the difference between these values being the error which it holds in one of its memories. This completes step 212 shown in FIG. 7. If this error is within acceptable limits already contained in one of the unit's memories as determined at step 214, the unit 110 will send a command signal to cease closure of the ink valve 26 so that filling of the cup 62 is resumed as indicated at step 216 at FIG. 7.

The central processing unit 110 then continues with that part of its program representing step 206 in FIG. 7, after a predetermined period.

If the error was not within the acceptable limits it calculates at step 214, in accordance with a formula which is already entered into the unit 110 as part of its pre-programming, a corresponding period for adding solvent to the ink. This is a step indicated at 218 in FIG. 7. Having made this calculation, the unit 110 will send via the buffer 118 and the address 122 a command for the solvent valve 36 to be opened. Solvent contained in the reservoir 32 may not flow, under the force of gravity, through the delivery tube 34 and the solvent valve 36 into the solvent feed pipe 40 down through the cup 62, the orifice 63, and into the tray 70 through the feed pipe 41 where it is then mixed in the ink already contained in the tank 10. The solvent valve 36 is held open in this way for the period determined at step 218 in FIG. 7, and this completes step 220 shown in FIG. 7. The unit 110 then sends a command signal for the ink valve 26 to be reopened, whereafter filling of the cup 62 is resumed, as indicated in step 222 at FIG. 7, The unit 110 now holds up the operating cycle of the apparatus for a "mean cycle period". This is calculated in accordance with a formula contained in the unit 110 as pre-programmed, and allows the solvent which has been added in this way to mix not only in the tank but also through the various flow tubes and pipes of the apparatus. This step is indicated at 224 in FIG. 7, and after the wait, the unit 110 continues with that part of its program corresponding to step 206 in FIG. 7.

It will be appreciated that the operation shown in FIG. 7 will maintain the vicsosity of the ink within predetermined limits, and solvent which naturally evaporates from the ink during the course of a printing process will be replenished by solvent added from the reservoir 32.

Figure 8:
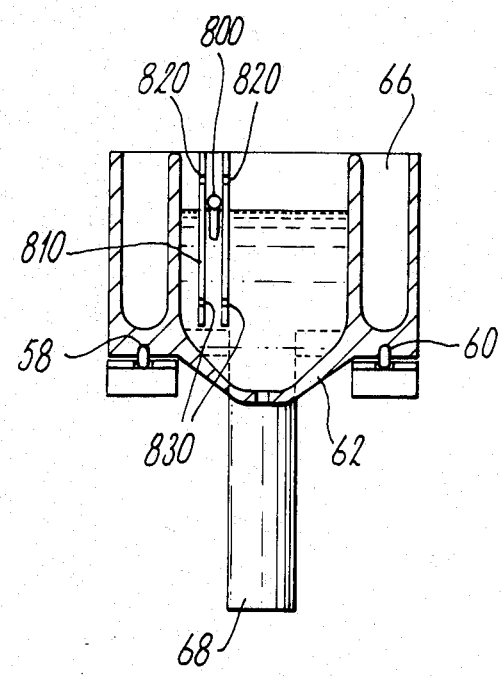
FIG. 8 is a cross-sectional view of a float to time the rate at which a cup empties.

Although the particular apparatus illustrated in the drawings uses an emitter-detector pair 54 and 56 to determine how long the cup 62 takes to empty, a measure of the viscosity of the ink could alternatively be obtained, for example, as shown in FIG. 8. A float 800 within a vertically extending tube 810 in the cup 62 is able to move up and down within the tube in accordance with the level of liquid in the cup 62. The float 800 is capable of closing an electrical connection between an upper pair of contacts 820, and then between a lower pair of contacts 830. The contact pairs 820 and 830 are connected to the buffer 118 shown in FIG. 6, and enable a count to be made of the time it takes for the float 800 to fall through a predetermined distance as the cup 62 is emptied, in particular the distance between the contact pairs 820 and 830.

It will be noted that, for most of the time during the operation of the apparatus, ink is continually flowing through various parts of the apparatus, and in particular the cup 62. This is important to ensure that the ink does not have an opportunity to coagulate, particularly not at the orifice 63 where such coagulation would give an incorrect reading for the viscosity of the ink. To reduce the likelihood of this occurring even further, the two-way valve 24 may be switched to allow fluid to flow from the solvent valve 36 through the ink valve 26, up the feed pipe 28 and into the cup 62 on depression of the "manual solvent" button 84.

Advantages of the illustrated apparatus may be as follows:

(i) It relieves the Printer of the viscosity control task for more important duties.
(ii) Basic operation of the apparatus is easy to follow.
(iii) Better accuracy is achieved.
(iv) Frequency of measurement is constant.
(v) When solvent addition is required, the microprocessor calculates the increase using information from previous additions.
(vi) Solvent is added and mixed automatically.
(vii) The apparatus makes direct measurements.

The electronics package contained in the microprocessor and control box can be designed around the plug-in board concept for ease of maintenance and total system integration. The operation of the control box is governed by one programmed memory I.C. Alteration of parameters, for example accuracy and tolerance limits, only requires a change in this one discrete component. Thus, specially programmed I.C.s for specialist jobs can be made for the customer with the minimum of system change and cost.

A wash cycle control button 900 shown in FIGS. 5 and 6 is operable to bring about (a) passage of solvent through the ink valve 26 by opening the passage from the solvent reservoir 32 shown in FIG. 1 to the ink valve 26 via the gravity feed tube 34, the solvent valve 36, the T-junction 38 and the two-way valve 24, and (b) stammering of the ink valve 26 to break away any hardened particles in or around the valve seating. The commands for bringing this about are stored as computer programs within the buffer 118, CPU 110, EPROM 112 and the RAMS 114 and 116. The ink pump 12 may be separately switched off for the wash cycle.

All the switches 80, 88, 102 and 900 may be covered by plastics membranes to protect them from splashes.

We claim:

1. A viscosimeter comprising a Zahn cup, supply means including a supply tank and a normally open valve in communication with the supply tank arranged to supply a liquid, the viscosity of which is to be measured, to the Zahn cup, control means operatively associated with the supply means to close the normally open valve to thereby stop the supply of the liquid to the Zahn cup at a point in time when the Zahn cup is overflowing, timing means operatively associated with the control means to initiate measuring the time taken for the Zahn cup to empty, the timing means comprising an emitter-detector pair positioned to direct a sensing beam across the flow path of the liquid which leaves the Zahn cup and a timer device connected to commence a time measurement at the instant the control means stops the supply of the liquid to the Zahn cup, and to stop the measurement at the instant the detector of the emitter-detector pair indicates an absence of the liquid therebetween, the control means reopening the normally open valve at a point in time after the timing means has stopped the measurement.

2. A viscosimeter according to claim 1 including means for mounting the Zahn cup and the emitter-detector pair so as to be precisely positioned in relation to one another to ensure that the sensing beam crosses the flow path of the liquid from the Zahn cup.

3. A viscosimeter according to claim 2, wherein the mounting means comprises locating means including two spigots on the Zahn cup which are received by a mounting bracket and an abutting surface below the level of the spigots prevents the cup from toppling over.

4. A viscosimeter according to claim 1, wherein the Zahn cup has a gutter or channel around its side to receive any liquid which overflows from the cup, and drainage means of the gutter or channel by which liquid can flow therefrom back to the supply tank.

5. A viscosimeter according to claim 1, wherein the control means is connected to a source of solvent liquid whereby such liquid can be passed through the control means to clean the latter.

6. A viscosimeter according to claim 5, wherein means are connected to the control means to make the latter stammer when solvent liquid is being passed therethrough, to assist in cleaning.

7. A viscosimeter according to claim 1, and including viscosity-changing means arranged to add viscosity-changing material to the liquid the viscosity of which is measured, in dependence upon the said time measurement.

8. A viscosimeter according to claim 7, wherein the said viscosity-changing means comprises solvent supply means arranged to supply solvent to the Zahn cup.

9. A method of measuring the viscosity of a liquid comprising supplying the liquid to a Zahn cup through a normally open valve in communication with a supply tank until the Zahn cup overflows, stopping the liquid supply by closing the normally open valve at a point in time when the Zahn cup is overflowing, initiating the measurement of the time taken for the Zahn cup to empty, the time measurement commencing at the instant when the liquid supply is stopped, and stopping the time measurement the instant the flow of the liquid from the Zahn cup ceases as detected by an emitter-detector pair positioned to direct a sensing beam across the flow path of the liquid which leaves the Zahn cup.

10. A viscosimeter comprising a Zahn cup, supply means including a supply tank and a normally opened valve in communication with the supply tank arranged to supply a liquid, the viscosity of which is to be measured, to the Zahn cup, control means operatively associated with the supply means to close the normally open valve to thereby stop the supply of the liquid to the Zahn cup at a point in time when the Zahn cup is overflowing, timing means arranged to measure the time taken for the liquid to flow out from the Zahn cup, the timing means comprising a float disposed in a vertically extending tube within the Zahn cup and adapted to move up and down within the tube in accordance with the level of the liquid in the Zahn cup, and a timer device connected to measure the time taken by the float to drop through the tube a predetermined distance as liquid leaves the Zahn cup, the timer device initiating timing responsive to the float passing an upper point along the tube and terminating timing responsive to the float passing a lower point along the tube, the distance between the upper and lower points comprising the predetermined distance during which time is measured.

11. The viscosimeter according to claim 10, wherein an upper pair of contacts is provided at the upper point along the tube and a lower pair of contacts is provided at the lower point along the tube, the float closing an electrical connection between the upper pair of contacts and then between the lower pair of contacts as the float falls through the predetermined distance, the closing of the electrical connection between the upper pair of contacts initiating timing and the closing of the electrical connection between the lower pair of contacts terminating timing by the timer device.

12. a viscosimeter comprising a Zahn cup, supply means arranged to supply a liquid, the viscosity of which is to be measured, to the Zahn cup, means for setting a desired viscosity for the liquid, control means operatively associated with the supply means to stop the supply of the liquid to the Zahn cup at a point in time when the Zahn cup is overflowing, means for determining the actual viscosity of the liquid including timing means operatively associated with the control means to measure the time taken for the level of the liquid in the Zahn cup to drop by a preselected distance, means for comparing the actual viscosity with the desired viscosity of the liquid, and means for automatically modifying the actual viscosity of the liquid to a value within predetermined acceptable limits of the desired viscosity of the liquid in the event the actual viscosity of the liquid is outside such limits.

13. A viscosimeter according to claim 12 wherein the means for setting the desired viscosity, means for comparing the actual viscosity with the desired viscosity, and means for automatically modifying the actual viscosity are contained in a control box.

14. A viscosimeter according to claim 13 wherein the control box includes a pre-programmed central processing unit, associated memories including an EPROM and a pair of RAMs connected to communicate with the central processing unit and with one another, and a buffer acting as an interface between the central processing unit and electrical signals from a portion of the timing means and the means for setting the desired viscosity.

15. A viscosimeter according to claim 14 wherein the buffer controls the means for automatically modifying the actual viscosity.

* * * * *